(12) United States Patent
Schäfer et al.

(10) Patent No.: US 10,017,466 B2
(45) Date of Patent: Jul. 10, 2018

(54) PROCESS FOR PURIFYING ASTAXANTHIN AND CANTHAXANTHIN

(71) Applicant: BASF SE, Ludwigshafen (DE)

(72) Inventors: Bernd Schäfer, Dierbach (DE); Wolfgang Siegel, Limburgerhof (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/516,216

(22) PCT Filed: Oct. 1, 2015

(86) PCT No.: PCT/EP2015/072685
§ 371 (c)(1),
(2) Date: Mar. 31, 2017

(87) PCT Pub. No.: WO2016/050909
PCT Pub. Date: Apr. 7, 2016

(65) Prior Publication Data
US 2017/0305850 A1    Oct. 26, 2017

(30) Foreign Application Priority Data
Oct. 2, 2014  (EP) .................................... 14187492

(51) Int. Cl.
C07C 403/24    (2006.01)

(52) U.S. Cl.
CPC ................................. *C07C 403/24* (2013.01)

(58) Field of Classification Search
USPC ......................................................... 568/361
See application file for complete search history.

(56) References Cited

U.S. PATENT DOCUMENTS

| | | |
|---|---|---|
| 4,212,827 A | 7/1980 | Paust et al. |
| 6,150,561 A | 11/2000 | Kreienbühl et al. |
| 6,590,111 B2 | 7/2003 | Grimmer et al. |
| 6,699,911 B2 | 3/2004 | Grimmer et al. |
| 7,329,789 B1 | 2/2008 | Schonemann et al. |

FOREIGN PATENT DOCUMENTS

| | | |
|---|---|---|
| CN | 102106448 A | 6/2011 |
| DE | 2534805 A1 | 2/1977 |
| EP | 0908449 A1 | 4/1999 |
| EP | 1197483 A2 | 4/2002 |
| EP | 1253131 A1 | 10/2002 |
| EP | 1285912 A2 | 2/2003 |
| WO | WO-0181301 A2 | 11/2001 |

OTHER PUBLICATIONS

International Search Report for PCT/EP2015/072685 dated Dec. 11, 2015.
Written Opinion of the International Searching Authority for PCT/EP2015/072685 dated Dec. 11, 2015.
*Carotenoids : vol. 2: Synthesis*; Britton G., Liaaen-Jensen, S., Eds.; Birkhäuser Verlag AG: Basel, 1996, pp. 11, 267-269, 281-286.
Choi, S., et al., "Efficient Syntheses of the Keto-carotenoids Canthaxanthin, Astaxanthin, and Astacene", Journal of Organic Chemistry, vol. 70, No. 8, (2005), pp. 3328-3331.
"Opinion of the Scientific Panel on Additives and Products or Substances used in Animal Feed on the request from the European Commission on the safety of use of colouring agents in animal nutrition; Part I. General Principles and Astaxanthin", EFSA Journal, vol. 291, (2005), p. 10.
Schäfer, B., Naturstoffe der chemischen Industrie [Natural materials of the chemical industry], Akademischer Verlag: Heidelberg, 2007, p. 423 ff.
Vine, A., et al., "Upregulation of Connexin 43 by Retinoids but Not by Non-Provitamin A Carotenoids Requires RARs", Nutrition and Cancer, vol. 52, No. 1, (2005), pp. 105-113.

*Primary Examiner* — Sikarl A Witherspoon
(74) *Attorney, Agent, or Firm* — Drinker Biddle & Reath LLP

(57) ABSTRACT

The present invention relates to a process for purifying the xanthophylls astaxanthin and canthaxanthin.
The process comprises suspending the xanthophyll in an organic solvent or solvent mixture, treating the suspension of the xanthophyll in the organic solvent or solvent mixture at elevated temperature, and subsequent separation off of the xanthophyll from the solvent by a solid-liquid separation, wherein the organic solvent is selected from ketones of the general formula (I) and mixtures of ketones of the general formula (I)

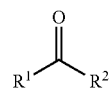

(I)

where $R^1$ is $C_1$-$C_4$ alkyl and $R^2$ is selected from $C_1$-$C_6$ alkyl, $C_3$-$C_8$ cycloalkyl, phenyl and benzyl, wherein the phenyl rings in the two last-mentioned radicals are unsubstituted or can have 1 or 2 methyl groups, or $R^1$ and $R^2$ together are linear $C_4$-$C_6$ alkylene, which can bear 1, 2 or 3 methyl groups as substituents.

21 Claims, No Drawings

PROCESS FOR PURIFYING ASTAXANTHIN AND CANTHAXANTHIN

CROSS-REFERENCE TO RELATED APPLICATIONS

This application is a national stage application (under 35 U.S.C. § 371) of PCT/EP2015/072685, filed Oct. 1, 2015, which claims benefit of European Application No. 14187492.5, filed Oct. 2, 2014, both of which are incorporated herein by reference in their entirety.

The present invention relates to a process for purifying the xanthophylls astaxanthin and canthaxanthin.

BACKGROUND OF THE INVENTION

Canthaxanthin (β,β-carotene-4,4'-dione) and astaxanthin (3,3'-dihydroxy-β,β-carotene-4,4'-dione) are red carotenoid pigments from the group of the xanthophylls which are described by the formula below (in each case the all-trans isomer is shown).

therefore has a chemoprotective action with respect to cancers (see A. L. Vine et al., Nutr. Cancer 52(1) (2005), 105-113).

Astaxanthin can be obtained on an industrial scale from blood-rain alga (*Haematococcus pluvialis*) or obtained from the shells of crustacia. Astaxanthin is generally obtained by extraction by means of dichloromethane (see, e.g. CN 102106448).

The production of synthetic astaxanthin, which is generally a mixture of the meso-(3R,3'S) form with the (3R,3'R)- and (3S,3'S) isomers is extensively described in the literature, e.g. in the monograph G. Britton, S. Liaanen-Jensen, H. Pfander (editors), Carotenoids, Vol. 2, Birkhauser Verlag, Basle, 1996, in particular p. 11, pp. 267 ff. and pp. 281 ff. and literature cited there, in various textbooks, such as B. Schäfer, Naturstoffe der chemischen Industrie [Natural materials of the chemical industry], Akademischer Verlag, Heidelberg, 2007, 427 ff. and literature cited there, and also in the patent literature, e.g. EP 1197483 or EP 1285912. Processes for producing canthaxanthin are described in the

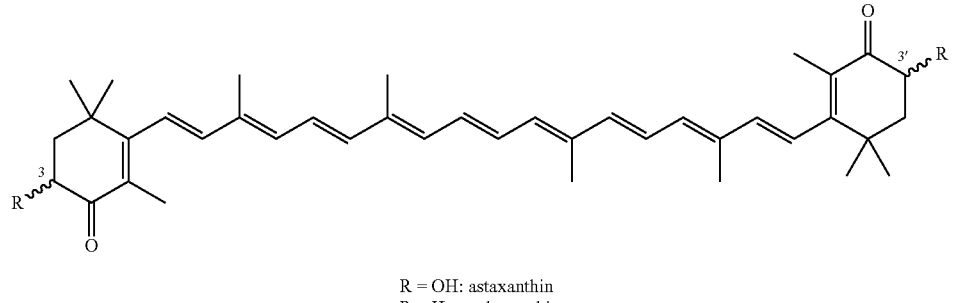

R = OH: astaxanthin
R = H: canthaxanthin

Astaxanthin, hereinafter also AXT, in contrast to canthaxanthin, has a center of asymmetry in the 3- and 3'-position and can therefore be present as a diastereomeric mixture of the (3R,3'R)-, (3S,3'S)- and (3S,3'R)-isomers, as a racemate of the (3R,3'R)- and the (3S,3'S)-isomer or in the form of the pure isomers. Synthetic AXT is frequently a mixture of the diastereomers (3S,3'S), (3R,3'S) and (3R,3'R). AXT obtained from natural sources can, depending on the respective natural source, be present in virtually pure (3S,3'S) or (3R,3'R) form. Likewise, enantiomerically pure astaxanthin is accessible by total synthesis.

Astaxanthin and canthaxanthin are primarily used as feed component for various animals, in particular for salmon and trout. Thus AXT has a vitamin-like activity acting as a result beneficially on the fertility and immune defense of the fish in breeding farms. Astaxanthin and canthaxanthin are permitted as feed additives to the fish food during the production of edible fish. Canthaxanthin and astaxanthin, however, are also used as food dyes, as nutriceuticals or cosmetics additives having antioxidant properties. AXT can protect the skin against the stress caused by UV radiation and acts in this function considerably more strongly than vitamin E. AXT supplements the protective action of sunscreen agents and cannot be washed off. Studies on animals permit the hypothesis that AXT lowers the blood sugar level and improves various parameters of the metabolic syndrome. In addition, in blood hypertension models, it leads to an increase in blood flow and of vascular tone. In addition, AXT appears to promote the formation of Connexin 43 and monograph G. Britton, S. Liaanen-Jensen, H. Pfander (editors), Carotenoids, Vol. 2, Birkhäuser Verlag, Basle, 1996, in particular p. 11, pp. 267 ff. and pp. 281 ff. and literature cited there, and also in Seyoung Choi et al., J. Org. Chem., 2005, 70 (8), p. 3328-333.

Astaxanthin and canthaxanthin have only low solubility in most organic solvents. The octanol-water partition coefficients log P (octanol/water) are in the same range: The log P of astaxanthin is 13,27 (The EFSA Journal 2005, 291, p. 10), the log P of canthaxanthin is 9,79 (FooDB data base, entry FDB015890) in contrast, their solubility in halogenated hydrocarbons such as dichloromethane or chloroform is adequate for many purposes. Therefore, the synthetic production of astaxanthin proceeds, at least in the final step, in a halogenated hydrocarbon such as dichloromethane, dichloroethane, chlorobenzene, trichloromethane, tetrachloroethane, tetrachloroethene or trichloroethane. Generally, halogenated hydrocarbons such as dichloromethane, dichloroethane or trichloromethane are used in the extraction of astaxanthin from natural sources. Therefore, astaxanthin generally comprises significant amounts of halogenated hydrocarbon as contaminants, which cannot be removed with usual auxiliaries. Halogenated hydrocarbons, however, are of toxicological concern. For many applications, in particular in those for pharmaceutical purposes, or for use in foods, strict limiting values with respect to halogenated hydrocarbons must be maintained. For instance, for example the content of dichloromethane in astaxanthin or canthaxanthin for many applications must not exceed a value of 600 ppm. For other halogenated hydrocarbons, likewise strict limiting values apply. Despite their comparatively high volatility, halogenated hydrocarbon contaminants in astaxanthin and canthaxanthin may be removed only with difficulty.

Further contaminants which occur, in particular, in the case of synthetic astaxanthin are organophosphorus compounds, in particular triphenylphosphine oxide, since many production methods comprise a Wittig reaction or a Horner-Emmons reaction. Thus, in industrial synthesis, astaxanthin is predominantly produced by reacting [5-(4-hydroxy-2,6,6-trimethyl-3-oxo-1-cyclohexyl)-3-methyl-2,4-pentadienyl] triphenylphosphonium bromide or a corresponding Horner-Emmons derivative with 2,7-dimethyloctatrienedial, C10-dialdehyde, wherein triphenylphosphine oxide or, in the case of the Horner-Wadsworth-Emmons variant, the corresponding phosphonate is formed. The production of astaxanthin by reacting a 3-[5-(arylsulfonyl)-4-methylpenta-1,3-dienyl]-6-hydroxy-2,4,4-trimethyl-cyclohex-2-en-1-one with C10-dialdehyde in the context of a Julia-olefination, is likewise known in the literature (see G. Britton et al. loc. cit., p. 12 and pp. 103 ff.). Further contaminants might be canthaxanthin isomers, echinenone and other colored carotenoid impurities. Canthaxanthin isomers are e.g. 9Z-Canthaxanthin and 13Z-Canthaxanthin. Other colored carotenoid impurities are e.g. β-Carotene and β-Carotene derived degradation products with $\lambda_{max}$ in the range from 400 to 700 nm.

Comparable production processes are known for canthaxanthin, e.g. the reaction of [5-(2,6,6-trimethyl-3-oxo-1-cyclohexyl)-3-methyl-2,4-pentadienyl]triphenylphosphonium bromide or a corresponding Horner-Emmons derivative with C10-dialdehyde and also the reaction of 3-[5-(arylsulfonyl)-4-methylpenta-1,3-dienyl]-2,4,4-trimethylcyclohex-2-en-1-one with C10-dialdehyde in the context of a Julia-olefination. The production of canthaxanthin by reacting β-carotene with oxidizing agents (see, e.g. DE 2534805 and literature cited there) is likewise known.

SUMMARY OF THE INVENTION

Surprisingly, it has been found that, by treating a suspension of astaxanthin or canthaxanthin in a ketone solvent of the general formula (I) or of mixtures of ketones of the general formula (I) as defined hereinafter at elevated temperature, and subsequent separation of the xanthophyll from the ketone solvent by a solid-liquid separation, solvent contaminants, in particular the halogenated hydrocarbons, but also other organic solvents such as tetrahydrofuran, dioxane, ethyl acetate or acetonitrile can be efficiently removed. At the same time, in this manner, the depletion of phosphorus-comprising compounds such as triphenylphosphine, triphenylphosphine oxide also succeeds. Likewise, the depletion of canthaxanthin isomers, echinenon and other colored carotenoid impurities from the xanthophylls and especially from canthaxanthin can also be achieved. This is surprising, since the inventors' own studies have found that it is not possible with many current solvents such as $C_1$-$C_3$-alkanols or supercritical $CO_2$, to reduce the content of halogenated hydrocarbons in AXT or other xanthophylls such as canthaxanthin to the required threshold values.

Accordingly, the present invention relates to a process for purifying the xanthophylls astaxanthin and canthaxanthin, comprising a) suspending the xanthophyll in an organic solvent or solvent mixture
b) treating the suspension of the xanthophyll in the organic solvent or solvent mixture at elevated temperature, and c) subsequent separation off of the xanthophylls from the solvent by a solid-liquid separation, wherein the organic solvent is selected from ketones of the general formula (I) and mixtures of ketones of the general formula (I)

where $R^1$ is $C_1$-$C_4$ alkyl and $R^2$ is selected from $C_1$-$C_6$ alkyl, $C_3$-$C_8$ cycloalkyl, phenyl and benzyl, wherein the phenyl rings in the two last-mentioned radicals are unsubstituted or can have 1 or 2 methyl groups or 1 or 2 ethyl groups, or $R^1$ and $R^2$ together are linear $C_4$-$C_6$ alkanediyl, which can bear 1, 2 or 3 methyl groups as substituents, and wherein the ketone of the formula (I) makes up at least 95% by weight of the organic solvents used for suspending the xanthophyll.

The process described hereinafter is applicable not only to the E-isomers of the xanthophylls, but also to various Z-isomers.

Preferred embodiments of the process according to the invention are presented in the claims of the present application.

The process is linked to a number of advantages. For instance, it is possible in an efficient manner to lower the content of halogenated hydrocarbons in the xanthophylls astaxanthin and/or canthaxanthin to the required toxicological threshold values or below. This reduction succeeds advantageously with good recovery rates of purified xanthophyll. In addition, at the same time, an efficient reduction of the content of organophosphorus compounds is observed.

The present invention also relates to the use of the process described herein for depleting halogenated hydrocarbons and/or phosphorus compounds from the xanthophylls astaxanthin and/or canthaxanthin which comprise halogenated hydrocarbons and/or phosphorus compounds as contaminants. In particular, the present invention relates to the use of the process described here for the simultaneous depletion of halogenated hydrocarbons and phosphorus compounds from the xanthophylls astaxanthin and/or canthaxanthin. Furthermore, the present invention also relates to the use of the process described herein for the at least one of the following impurities from xanthophylls: canthaxanthin isomers, echinenone and/or other colored carotenoid impurities.

MORE DETAILED DESCRIPTION OF THE INVENTION

Here and hereinafter, the prefix $C_n$-$C_m$ indicates the number of carbon atoms which a molecule denoted therewith, or a radical denoted therewith, can have.

For instance, $C_1$-$C_4$ alkyl is a linear or branched, saturated aliphatic hydrocarbon radical having 1 to 4 carbon atoms, for example methyl, ethyl, n-propyl, isopropyl, n-butyl, 2-butyl, isobutyl or tert-butyl (=2-methyl-2-propyl). Correspondingly, $C_1$-$C_6$ alkyl is a linear or branched, saturated aliphatic hydrocarbon radical having 1 to 6 carbon atoms, for example one of the radicals cited under $C_1$-$C_4$ alkyl, and also n-pentyl, 2-pentyl, 2-methyl-1-butyl, 3-methyl-1-butyl, 2-methyl-2-butyl, 3-methyl-2-butyl, 2,2-dimethylpropyl, n-hexyl, 2-hexyl, 2-methyl-1-pentyl, 3-methyl-1-pentyl, 2-methyl-2-pentyl, 2-methyl-3-pentyl, 3-methyl-3-pentyl, 2,2-dimethylbutyl, 2,3-dimethylbutyl or 3,3-dimethylbutyl.

$C_3$-$C_6$ Cycloalkyl is a saturated alicyclic hydrocarbon radical having 3 to 6 carbon atoms, for example cyclopropyl, cyclobutyl, cyclopentyl or cyclohexyl.

Linear $C_4$-$C_6$ alkanediyl is a saturated unbranched bivalent hydrocarbon radical having 4 to 6 carbon atoms, for example 1,4-butanediyl, 1,5-pentanediyl or 1,6-hexanediyl.

Where used, aryl is phenyl that can be substituted by 1, 2 or 3 identical or different radicals which are selected from $C_1$-$C_4$ alkyl and especially from methyl and ethyl.

The descriptions given here and hereinafter on the conditions of purification and the solvents of the formula (I) used and also on embodiments of, and modes of carrying out, the process according to the invention apply identically to astaxanthin and canthaxanthin. They apply, in particular, when astaxanthin is used as xanthophyll that is to be purified, the purification of which is a preferred embodiment of the process according to the invention.

In the process of the invention, the respective xanthophyll, i.e. astaxanthin or canthaxanthin, is suspended in a ketone of the formula (I) or mixture of ketones of the formula (I). Preference is given to those ketones where $R^1$ and $R^2$ and, in particular in combination, have the following meanings:

$R^1$ is, in particular, methyl or ethyl $R^2$ is, in particular, $C_1$-$C_4$ alkyl, especially methyl or ethyl.

Examples for ketones of the formula I are acetone (2-propanone), methyl ethyl ketone (MEK; 2-butanone), diethyl ketone (DEK; 3-pentanone), methyl isobutyl ketone (MIBK), 2-pentanone, 3-methylbutanone, cyclopentanone and cyclohexanone.

The ketone or the ketones of the formula (I) make up at least 95% by weight, in particular at least 99% by weight, of the organic solvents used for the suspension. Preferably, the organic solvent or solvent mixture used to produce the suspension comprises substantially no halogenated alkanes, in particular less than 1000 ppm, and especially less than 500 ppm, of halogenated alkanes. These apply correspondingly to the phosphorus contaminants. Preferably, the organic solvent or solvent mixture used to produce the suspension comprises no, or only small amounts of less than 1% by weight, of organic solvents, which are different from the ketones of the formula (I). These include $C_1$-$C_4$ alkanols such as methanol, ethanol, n-propanol or isopropanol, cyclic and acyclic aliphatic ethers such as diethyl ether, methyl tert-butyl ether, diisopropyl ether, tetrahydrofuran or dioxane, and in addition esters of aliphatic carboxylic acids such as ethyl acetates and also acetonitrile.

The solvent of the formula (I) or solvent mixture thereof used to produce the suspension can comprise water or be substantially anhydrous. The concentration of water in the solvent used to produce the suspension, however, frequently will not exceed 20% by weight, and especially will not exceed 10% by weight. Frequently, to produce the suspension a solvent of the formula (I), or a solvent mixture thereof, is used which comprises less than 2% by weight of water. However, it is also possible to use a solvent of the formula (I) or a solvent mixture thereof that comprises more than 2% by weight of water.

In a special embodiment, acetone is used as sole solvent of the formula (I), or a solvent mixture of solvents of the formula (I) is used which comprises at least 80% by weight, in particular at least 90% by weight, acetone and up to 20% by weight, in particular up to 10% by weight, of a solvent of the formula (I) that is different from acetone, wherein the solvent of the formula (I) that is different from acetone is selected, in particular, from ketones of the formula (I), where $R^1$ is methyl or ethyl, and $R^2$ is selected from $C_2$-$C_4$ alkyl.

The suspension preferably has a concentration of the xanthophylls astaxanthin or canthaxanthin in the range from 2 to 50% by weight, in particular in the range from 5 to 40% by weight, and especially in the range from 10 to 20% by weight, in each case based on the total weight of the suspension.

Here and hereinafter, the expression "at elevated temperature" means at a temperature of at least 60° C., in particular at least 80° C. and especially at least 90° C.

In order to achieve an efficient depletion of the contaminants from the xanthophyll, the suspension of the xanthophyll is preferably treated at a temperature in the range from 60 to 150° C., in particular in the range from 80 to 120° C., especially in the range from 90 to 110° C.

The treatment can be carried out unpressurized or under pressure, wherein the pressure in the treatment vessel will preferably not exceed 10 bar. Preferably, the treatment proceeds at the inherent pressure of the solvent which is established in a closed treatment vessel at the treatment temperature.

For depletion of the contaminants from the xanthophyll, it can be advantageous if, during the treatment, some of the solvent for solvent mixture is removed by distillation and replaced by fresh solvent of the formula (I). For example, during the treatment, 5 to 90% by weight of the solvent or solvent mixture can be distilled off and replaced by fresh solvent. The quantitative ratio of solvent distilled off to fresh solvent can be varied, wherein, preferably, no more fresh solvent is added and corresponds to the amount of solvent distilled off. Of course, the amount of fresh solvent added can be less than the amount of solvent distilled off, in order in this manner to concentrate the suspension. In particular, the ratio of solvent distilled off to freshly added solvent is then in the range from 1:1 to 10:1.

The treatment of the suspension at elevated temperature proceeds, preferably, with mixing or agitation of the suspension, for example by shaking or stirring the suspension.

The treatment of the suspension at elevated temperature can be carried out discontinuously in the batch mode or semi-batch mode, or continuously. Devices suitable therefor are known to those skilled in the art. In the case of a discontinuous reaction procedure, the treatment usually proceeds in a reaction kettle which can be equipped with means for mixing the suspension, for example stirrer or circulation pump. The continuous treatment can be carried out in a manner known per se in stirred-tank cascades or tubular reactors.

The treatment time, i.e. the time of action of the ketone or ketone mixture at the elevated temperature which is necessary for a depletion of the contaminant(s) under the desired threshold value or values of course depends on the concentration of the contaminant in the xanthophyll, the type of contaminant, the permissible toxicological threshold value and the temperature of the treatment. The required time can be determined by serial experiments or by sampling. The treatment time will generally be at least 1 h. The upper limit of the treatment time is generally determined by economic factors and can, if desired, also be up to several days or a week. Preferably, the entire treatment time is at least 6 h, in particular at least 12 h, and especially at least 24 h and is, for example, in the range from 6 to 144 h, in particular in the range from 12 to 120 h, and especially in the range from 24 to 96 h.

Subsequent to the treatment, the xanthophyll is separated off, especially the astaxanthin, from the solvent mixture. The separating off process proceeds naturally by a solid-liquid separation in a manner known per se, for example by a filtration or centrifugation, or a combination of these measures. To avoid losses of yield, it has proven useful to carry out the solid-liquid separation at low temperatures, preferably at temperatures of a maximum of 20° C., in particular a maximum of 10° C., especially a maximum of 0° C., e.g. at a temperature in the range from −20 to +20° C., in particular in the range from −10 to +10° C., especially in the range from −10 to 0° C. Preferably, the suspension will preferably be cooled before the solid-liquid separation is carried out, to a temperature of a maximum of 20° C., in particular a maximum of 10° C., in particular a maximum of 0° C. The temperature limit to which the suspension is cooled will usually not exceed −20° C., in particular −10° C. Preferably, it is possible to cool the device in which the solid-liquid separation of the purified xanthophyll is performed.

The purified xanthophyll, especially astaxanthin, arising in the solid-liquid separation can be washed with fresh solvent of the formula (I) to remove adhering solvent residues. Preferably, the washing proceeds at a temperature in the range from −20 to +20° C., in particular in the range from −10 to +10° C., especially in the range from −10 to 0° C. Preferably, the amount of solvent of the formula (I) used for the washing will not make up more than 10 parts by weight, e.g. 1 to 10 parts by weight, in particular 3 to 5 parts by weight, relative to 1 part by weight of xanthophyll.

The purified xanthophyll, especially astaxanthin, arising in the solid-liquid separation can then be dried and confected. The drying proceeds in a manner known per se, preferably in a nitrogen stream or at reduced pressure, wherein, preferably, a temperature in the range from 20 to 100° C. is used for the drying.

The purified xanthophyll, especially astaxanthin, occurring in the solid-liquid separation can also again be suspended in the solvent of the formula (I) or mixture of solvents of the formula (I) and the suspension can again be subjected to a treatment at elevated temperature. In this manner, generally, further depletion of the xanthophyll-comprising contaminants succeeds. The process according to the invention can accordingly comprise one, or preferably a plurality of, treatment cycles. A treatment cycle is taken to mean treatment of the suspension in the solvent or solvents of the formula (I) and the subsequent solid-liquid separation of the xanthophyll. Preferably, the treatment comprises at least 2, in particular at least 3, treatment cycles, e.g. 2 to 6 cycles, in particular 3 to 5 cycles.

If the treatment comprises a plurality of treatment cycles, the respective cycle will be carried out in the above described manner. The conditions under which the treatment cycles are carried out correspond to the above described conditions. However, it is not required that the condition of successive cycles are identical. Rather, the conditions employed in the respective cycles such as treatment time, temperature, pressure, concentration, solvent used, solid-liquid separation etc., can be varied. Preferably, with respect to the parameters temperature, pressure, concentration, solvent used, and solid-liquid separation, the conditions cited above as preferred can be employed. In contrast, the treatment time of a single cycle is selected in such a manner that the total time of all treatment cycles is at least 6 h, in particular at least 12 h, and especially at least 24 h, and is, for example, in the range from 6 to 144 h, in particular in the range from 12 to 120 h, and especially in the range from 24 to 96 h. The treatment time of one cycle is preferably in the range from 1 to 48 h, in particular in the range from 6 to 36 h, and especially in the range from 12 to 30 h.

In a preferred embodiment of the invention, first a suspension of the xanthophyll, especially the astaxanthin, will be treated at elevated temperature in one or more cycles, e.g. 1, 2, 3 or 4 cycles, in a ketone of the formula (I), where $R^1$ is methyl or ethyl, and $R^2$ is $C_2$-$C_4$ alkyl, e.g. in diethyl ketone, methyl isobutyl ketone or methyl ethyl ketone, and the xanthophyll thus obtained will be treated with acetone in one or more cycles, preferably in 1 or 2 cycles.

The xanthophyll, especially astaxanthin, that is to be purified and is used in the process according to the invention of course comprises at least one amount that is to be depleted in an amount which exceeds the limiting value or threshold value desired or demanded for the desired application.

The xanthophyll, especially astaxanthin, that is to be purified and is used in the process according to the invention generally comprises at least one halogenated hydrocarbon, in particular one or more chlorinated hydrocarbons such as dichloromethane, dichloroethane, chlorobenzene, trichloromethane, trichloroethane, tetrachloroethane or tetrachloroethene. The content of halogenated hydrocarbon, in particular one or more chlorinated hydrocarbons such as dichloromethane, dichloroethane, chlorobenzene, trichloromethane, trichloroethane, tetrachloroethane or tetrachloroethene is frequently at least 500 ppm, in particular at least 1000 ppm, especially at least 1500 ppm, e.g. 1000 to 10 000 ppm, or 1500 to 5000 ppm.

The xanthophyll that is to be purified and is used in the process according to the invention can be a synthetic xanthophyll or a xanthophyll from natural sources. Preferably, it is a synthetic xanthophyll, in particular a xanthophyll, in the synthesis of which, in particular in the last stage of the synthesis, a Wittig reaction or Horner-Wadsworth-Emmons reaction or a Julia reaction is carried out. A xanthophyll produced in this manner generally comprises organic phosphorus compounds such as triphenylphosphine or triphenylphosphine oxide, if the synthesis comprises a Wittig reaction or Horner-Wadsworth-Emmons reaction.

In specific embodiments of the process according to the invention, an astaxanthin is used which was produced by Wittig reaction of a [5-(4-hydroxy-2,6,6-trimethyl-3-oxo-1-cyclohexyl)-3-methyl-2,4-pentadienyl]triphenylphosphonium salt, in particular of the bromide, with 2,7-dimethyloctatrienedial. Such an astaxanthin comprises production-related triphenylphosphine and/or triphenylphosphine oxide.

In a further specific embodiment of the process according to the invention, an astaxanthin is used which was produced by Julia reaction of a 3-[5-(arylsulfonyl)-4-methylpenta-1,3-dienyl]-6-hydroxy-2,4,4-trimethylcyclohex-2-en-1-one with 2,7-dimethyloctatrienedial.

In further specific embodiments of the process according to the invention, a canthaxanthin is used which was produced by Wittig reaction of a [5-(2,6,6-trimethyl-3-oxo-1-cyclohexyl)-3-methyl-2,4-pentadienyl]triphenylphosphonium salt, in particular of the bromide with 2,7-dimethyloctatrienedial. Such a canthaxanthin contains production-related triphenylphosphine and/or triphenylphosphine oxide.

In a further specific embodiment of the process according to the invention, a canthaxanthin is used which was produced by Julia reaction of a 3-[5-(arylsulfonyl)-4-methylpenta-1,3-dienyl]-2,4,4-trimethylcyclohex-2-en-1-one with 2,7-dimethyloctatrienedial.

In a further specific embodiment of the process according to the invention, a canthaxanthin is used which was produced by oxidation of β-carotene.

In a group of embodiments of the process according to the invention, the xanthophyll that is to be purified comprises, in particular, one or more organic phosphorus compounds, in particular triphenylphosphine and/or triphenylphosphine oxide. The phosphorus content in such a xanthophyll is generally at least 20 ppm, frequently at least 50 ppm, and can be lowered by the process according to the invention to a value below 20 ppm, in particular below 10 ppm. The phosphorus content cited here is the content based on elemental phosphorus.

In a further group of embodiments of the process according to the invention, xanthophyll, especially the canthaxanthin, that is to be purified contains at least one impurity selected from canthaxanthin isomers, echinenone and/or other colored carotenoid impurities. Canthaxanthin isomers are e.g. 9Z-Canthaxanthin and 13Z-Canthaxanthin. Other colored carotenoid impurities are e.g. β-Carotene and β-Carotene derived degradation products with $\lambda_{max}$ in the range from 400 to 700 nm.

The xanthophyll used for producing the suspension, in particular the astaxanthin that is preferably used, can be crystalline, semicrystalline or amorphous, wherein crystalline forms are preferred. Frequently, the astaxanthin preferably used in the process according to the invention is a synthetic diastereomer mixture, in particular a mixture of the diastereomers (3S,3'S), (3R,3'S) and (3R,3'R).

The xanthophyll that is used to produce the suspension is generally a powder, preferably a powder having weight-average particle sizes determined by laser diffraction in the range from 5 to 100 μm. In particular, the powder has a $d_{90}$ value below 150 μm.

EXAMPLES

The following abbreviations are used
DEK: Diethyl ketone
DCM: Dichloromethane
MIBK: Methyl isobutyl ketone
ppm: parts per million The starting material used was an astaxanthin powder which had been produced by Wittig reaction of [5-(4-hydroxy-2,6,6-trimethyl-3-oxo-1-cyclohexyl)-3-methyl-2,4-pentadienyl]triphenylphosphonium bromide with 2,7-dimethyloctatrienedial according to the synthesis described in G. Britton, S. Liaanen-Jensen, H. Pfander (editors), Carotenoids, Vol. 2, Birkhäuser Verlag, Basle, 1996, pp. 283 ff. and the literature cited there.

The solvent content in the astaxanthin was determined by means of headspace gas chromatography: for this purpose 50 mg of the astaxanthin were placed in a closed sample vessel. The sample vessel was heated to 80° C. and, after 1 h, a sample was withdrawn and analyzed by gas chromatography by means of a DB-624-capillary (30 m) from Agilent with a temperature gradient from 40 to 200° C.

The phosphorus content was determined by means of atomic absorption spectrometry.

The contents of canthaxanthin isomers, echinenone, and other colored carotenoid impurities were determined by means of HPCL.

Example 1: Purification with Acetone

In a pressure container, 200 g of astaxanthin were suspended in 1100 g of acetone at 20 to 25° C. The suspension was heated at 100° C. under the inherent pressure (approximately 4 bar) for 20 h with stirring. Subsequently, the mixture was cooled to 0° C. and the suspension was filtered. The filtercake was washed three times with acetone at 0° C. (1st cycle). The filtercake was again suspended in acetone and the suspension was heated at 100° C. for 24 h in the manner described for the 1st cycle and after cooling was filtered and washed with cold acetone (2nd cycle). This was repeated a further two times (3rd and 4th cycles). After the fourth filtration, the solids were dried to constant weight in a nitrogen stream at 20° C. 160 g (80% yield) of pure astaxanthin were obtained. After each cycle, a sample was withdrawn and after the drying (20° C., nitrogen steam, constant weight), the content of phosphorus and the content of solvent were determined. The analytical data of the starting material and after the respective cycles are summarized in the table below.

|  |  | Headspace GC [ppm] | | Phosphorus |
|---|---|---|---|---|
|  | Drying | Acetone | DCM | [ppm] |
| Starting material |  | 20 | 1900 | 100 |
| 1st cycle | N₂ stream | 1700 | 1000 | 15 |
| 2nd cycle | N₂ stream | 1500 | 400 | 9 |
| 3rd cycle | N₂ stream | 1900 | 200 | 5 |
| 4th cycle | N₂ stream | 1500 | 130 | 3 |

Example 2: Purification with Diethyl Ketone

In a manner similar to example 1, the experiment was carried out using diethyl ketone unpressurized under reflux at 102° C. The yield of pure astaxanthin was likewise 80%. The analytical data of the starting material and after the respective cycles are summarized in the following table.

|  |  | Headspace GC [ppm] | | Phosphorus |
|---|---|---|---|---|
|  | Drying | DEK | DCM | [ppm] |
| Starting material |  | 0 | 2000 | 100 |
| 1st cycle | N₂ stream | 1600 | 490 | 10 |
| 2nd cycle | N₂ stream | 1500 | 120 | 5 |
| 3rd cycle | N₂ stream | 1500 | <100 | 3 |
| 4th cycle | N₂ stream | 1800 | <100 | 3 |

Example 3: Purification Using Isobulyl Methyl Ketone

In a manner similar to example 1, the experiment was carried out using isobutyl ethyl ketone unpressurized at 100° C. The yield of pure astaxanthin was likewise 80%. The analytical data of the starting material and after the respective cycles are summarized in the following table.

|  |  | Headspace GC [ppm] | | Phosphorus |
|---|---|---|---|---|
|  | Drying | MIBK | DCM | [ppm] |
| Starting material |  | 0 | 2000 | 100 |
| 1st cycle | N₂ stream | 2200 | 2000 | 20 |
| 2nd cycle | N₂ stream | 2400 | 510 | 10 |
| 3rd cycle | N₂ stream | 2600 | 260 | 7 |
| 4th cycle | N₂ stream | 2400 | 160 | 5 |

Example 4: Purification Using Diethyl Ketone with Distillation

Example 2 was repeated using a 15% strength suspension of astaxanthin in diethyl ketone, wherein the suspension was heated for 4 days under reflux and each day 20% of the diethyl ketone was distilled off and replaced by the same amount of fresh diethyl ketone. On the fourth day, the suspension was cooled to 0° C. and the solids were filtered off. The solids were washed three times with diethyl ketone at 0° C. and then dried in a nitrogen stream at 20° C. The yield of pure astaxanthin was 85 to 90%. The analytical data of the starting material and the treatment are summarized in the following table.

|  | Drying | Headspace GC [ppm] DEK | Headspace GC [ppm] DCM | Phosphorus [ppm] |
|---|---|---|---|---|
| Starting material |  | 0 | 2000 | 100 |
| 96 h, 102° C. | N₂ stream | 1600 | 400 | 10 |

Example 5: Purification of Astaxanthin with Cyclohexanone

A suspension of 30 g astaxanthin in 170 g cyclohexanone was heated to 100° C. for 20 h. Subsequently, the mixture was cooled to 0° C. and the suspension was filtered. The filtercake was washed 3 times with cyclohexanone (25 ml each time) and then dried. 22.5 g of product were obtained.

| Astaxanthin | Phosphorus [ppm] |
|---|---|
| Starting material | 100 |
| Product | 21 |

Example 6: Purification of Astaxanthin with Acetophenone

A suspension of 30 g astaxanthin in 170 g acetophenone was heated to 100° C. for 20 h. Subsequently, the mixture was cooled to 0° C. and the suspension was filtered. The filtercake was washed 4 times with acetone (50 ml each time) and dried. 21.1 g of product were obtained.

| Astaxanthin | Phosphorus [ppm] |
|---|---|
| Starting material | 100 |
| Product | 7 |

Example 7: Purification of Canthaxanthin with Acetone

A suspension of 75 g canthaxanthin in 425 g acetone was heated under inherent pressure to 100° C. for 20 h. Subsequently, the mixture was cooled to 0° C. and the suspension was filtered. The filtercake was washed 3 times with acetone (100 ml each time) and dried. 55.9 g of product were obtained.

| Canthaxanthin | Canthaxanthin isomers (HPLC a %) | Echinenone (HPLC a %) | Other colored carotenoid impurities (HPLC a %) |
|---|---|---|---|
| Starting material | 5.73 | 2.98 | 0.44 |
| Product | 3.32 | 2.41 | 0.18 |

Example 8: Purification of Canthaxanthin with Diethylketone

A suspension of 30 g canthaxanthin in 170 g diethylketon was heated to 100° C. for 20 h. Subsequently, the mixture was cooled to 0° C. and the suspension was filtered. The filtercake was washed 3 times with diethylketone (25 ml each time) and dried. 35.06 g of product were obtained.

| Canthaxanthin | Canthaxanthin-Isomers (HPLC a %) | Echinenone (HPLC a %) | Other colored carotenoid impurities (HPLC a %) |
|---|---|---|---|
| Starting material | 5.73 | 2.98 | 0.44 |
| Product | 1.75 | 1.41 | 0 |

Example 9: Purification of Canthaxanthin with Isobutylmethylketone

A suspension of 30 g canthaxanthin in 170 g isobutylmethylketone was heated to 100° C. for 20 h. Subsequently, the mixture was cooled to 0° C. and the suspension was filtered. The filtercake was washed 3 times with isobutylmethylketone (25 ml each time) and dried. 32.2 g of product were obtained.

| Canthaxanthin | Canthaxanthin isomers (HPLC a %) | Echinenone (HPLC a %) | Other colored carotenoid impurities (HPLC a %) |
|---|---|---|---|
| Starting material | 5.73 | 2.98 | 0.44 |
| Product | 2.46 | 1.83 | 0.14 |

The invention claimed is:

1. A process for purifying a xanthophyll selected from the group consisting of astaxanthin and canthaxanthin, comprising
    a) suspending the xanthophyll in an organic solvent or solvent mixture,
    b) treating the suspension of the xanthophyll in the organic solvent or solvent mixture at elevated temperature, and
    c) subsequent separation off of the xanthophyll from the solvent by a solid-liquid separation,
    wherein the organic solvent is selected from ketones of the formula (I) and mixtures of ketones of the formula (I)

(I)

where $R^1$ is $C_1$-$C_4$ alkyl and $R^2$ is selected from $C_1$-$C_6$ alkyl, $C_3$-$C_8$ cycloalkyl, phenyl and benzyl, wherein the phenyl rings in the two last-mentioned radicals are unsubstituted, or R¹ and R² together are linear $C_4$-$C_6$ alkanediyl, which can bear 1, 2 or 3 methyl groups as substituents, wherein the ketone of the formula (I) makes up at least 95% by weight of the organic solvents used for suspending the xanthophyll, and wherein the suspension of the xanthophyll is treated at a temperature of at least 60° C. and for at least 1 h, and wherein the xanthophyll used comprises halogenated hydrocarbons and/or phosphorus compounds as contaminants which are depleted.

2. The process according to claim 1, wherein the ketone of the formula (I) makes up at least 99% by weight of the organic solvents used for the suspension.

3. The process according to claim 1, wherein the concentration of water in the solvent used to produce the suspension does not exceed 20% by weight.

4. The process according to claim 1, wherein the suspension is treated at a temperature in the range from 60 to 150° C.

5. The process according to claim 1, wherein the treatment time of treating the suspension is in the range from 6 to 144 h.

6. The process according to claim 1, wherein the suspension has a xanthophyll concentration in the range from 2 to 50% by weight.

7. The process according to claim 1, wherein, in the course of the treatment, at least some of the ketone of the formula (I) is distilled off and replaced by fresh ketone of the formula (I).

8. The process according to claim 1, wherein the suspension is cooled to a temperature below 20° C. before separating off the xanthophyll from the organic solvent.

9. The process according to claim 1, wherein the ketone is selected from compounds of the general formula (I) and mixtures thereof, where R¹ is methyl or ethyl and R² is $C_1$-$C_4$ alkyl.

10. The process according to claim 1, wherein a suspension of the xanthophyll in a ketone of the formula (I), where R¹ is methyl or ethyl and R² is $C_2$-$C_4$ alkyl, is first treated at elevated temperature and the xanthophyll thus obtained is treated with acetone.

11. The process according to claim 1, wherein the treatment of the suspension of the xanthophyll in the organic solvent and the subsequent separation off of the xanthophyll from the solvent is repeated at least once.

12. The process according to claim 1, wherein the xanthophyll used contains one or more halogenated hydrocarbons as contaminant.

13. The process according to claim 1, wherein the xanthophyll used comprises at least one organic phosphorus compound, as contaminant.

14. The process according claim 1, wherein the xanthophyll used is astaxanthin.

15. The process according to claim 14, wherein the astaxanthin used is an astaxanthin produced by Wittig reaction of [5-(4-hydroxy-2,6,6-trimethyl-3-oxo-1-cyclohexyl)-3-methyl-2,4-pentadienyl]triphenylphosphonium bromide or 3-[5-(arylsulfonyl)-4-methylpenta-1,3-dienyl]-6-hydroxy-2,4,4-trimethylcyclohex-2-en-1-one with 2,7-dimethyloctatrienedial.

16. The process according to claim 1, wherein the xanthophyll used is canthaxanthin.

17. The process according to claim 16, wherein the canthaxanthin used is a canthaxanthin produced by Wittig reaction of [5-(2,6,6-trimethyl-3-oxo-1-cyclohexyl)-3-methyl-2,4-pentadienyl]triphenylphosphonium bromide or 3-[5-(arylsulfonyl)-4-methylpenta-1,3-dienyl]-2,4,4-trimethylcyclohex-2-en-1-one with 2,7-dimethyloctatrienedial.

18. The process according to claim 1 wherein halogenated hydrocarbons and/or phosphorus compounds are depleted from xanthophylls selected from astaxanthin and canthaxanthin which comprise halogenated hydrocarbons and/or phosphorus compounds as contaminants.

19. The process according claim 1 wherein at least one of the following impurities is depleted from xanthophylls; canthaxanthin isomers, echinenone and other colored carotenoid impurities.

20. The process according to claim 1, wherein the xanthophyll used comprises triphenylphosphine or triphenylphosphine oxide, as contaminant.

21. The process according to claim 1 wherein the suspension of the xanthophyll is treated at a temperature of at least 80° C.

* * * * *